United States Patent [19]

Meek et al.

[11] Plant 4,696

[45] Apr. 21, 1981

[54] CHRYSANTHEMUM PLANT

[75] Inventors: Jack M. Meek; William E. Duffett, both of Salinas, Calif.

[73] Assignee: Yoder Brothers, Inc., Barberton, Ohio

[21] Appl. No.: 99,416

[22] Filed: Dec. 3, 1979

[51] Int. Cl.[3] ..... A01H 5/00
[52] U.S. Cl. ..... Plt./74
[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum cultivar particularly characterized as to uniqueness by the combined characteristics of flat capitulum form; daisy capitulum type; dark red ray floret color with minimum color oxidation, yellow green (immature) to yellow (mature) disc floret color; diameter across face of capitulum ranging from 90 to 100 mm. at maturity; uniform eight week photoperiodic flowering response to short days; tall plant height when grown as a single stem cut spray; and semi-upright branching pattern.

3 Drawing Figures

1

The present invention comprises a new and distinct cultivar of *Chrysanthemum morifolium,* Ramat., hereinafter referred to by the cultivar name Dragon.

Dragon is a product of a planned breeding program which had the objective of creating new chrysanthemum cultivars with daisy capitulum type, red and red-bronze ray floret color, eight week flowering response and with the ability to produce commercially acceptable quality in year round cut mum programs. Such traits in combination were not present in previously available commercial cultivars.

Dragon was originated in a controlled hybridization program in Salinas, Calif. in 1978. The female parent was an unnamed bronze-red daisy (#75146024) originated from a hybridization of Firepower, disclosed in U.S. Plant Pat. No. 3,947, and an unnamed seedling (#773176012). The male parent of Dragon was an unnamed pink daisy (#71363002) originated from a hybridization of Dramatic, disclosed in U.S. Plant Pat. No. 3,189, and Bonnie Jean (unpatented; commercially available).

Dragon was discovered and selected as one flowering plant within the progeny of the stated cross by Jack M. Meek and William E. Duffett on May 23, 1978 in a controlled environment in Salinas, Calif.

The first act of asexual reproduction of Dragon was accomplished when vegetative cuttings were taken from the initial selection in August, 1978 in a controlled environment in Salinas, Calif. by a technician working under formulations established and supervised by Jack M. Meek and William E. Duffett. Continued asexual reproduction by vegetative cuttings for evaluative tests in flowering and stock programs in conjunction with horticultural examination of selected plants initiated in February, 1979 has demonstrated that the combination of characteristics as herein disclosed for Dragon are firmly fixed and are retained through successive generations of asexual reproduction.

Dragon has not been observed under all possible environmental conditions. The phenotype may vary significantly with variations in environment such as temperature, light intensity and daylength. The following observations, measurements and comparisons describe plants grown in Salinas, Calif. under greenhouse

2 conditions which approximate those generally used in commercial practice.

The following traits have been repeatedly observed and are determined to be basic characteristics of Dragon which in combination distinguish this chrysanthemum as a new and distinct cultivar:

(1) flat capitulum form, (2) daisy capitulum type, (3) dark red ray floret color with minimum color oxidation, (4) yellow green (immature) to yellow (mature) disc floret color, (5) diameter across face of capitulum ranging from 90 to 100 mm. at maturity, (6) uniform eight week photoperiodic flowering response to short days, (7) tall plant height (attaining a height as a flowered plant of 60 to 70 cm. from a rooted cutting planted to short days for May through October flowerings), and (8) semi-upright branching pattern.

Of the many commercial cultivars known to the present inventors, the most similar in comparison to Dragon are Firepower and Red Dazzler, the latter being disclosed in U.S. Plant Pat. No. 3,523. Reference is made to attached Chart A which compares certain characteristics of Dragon to those same characteristics of Firepower and Red Dazzler.

General comparisons are as follows:

(1) In comparison to Firepower, Dragon has different ray floret color, larger diameter across face of capitulum, shorter plant height, and a shorter flowering response period. The capitulum form and capitulum type of Dragon are similar to those same characteristics of Firepower.

(2) In comparison to Red Dazzler, Dragon has different ray floret color, longer capitulum form retention, and larger diameter across face of capitulum. The capitulum form, capitulum type, plant height, and flowering response period of Dragon are similar to those same characteristics of Red Dazzler.

The accompanying photographic drawings show typical inflorescence and foliage characteristics of Dragon, with the colors being as nearly true as possible with illustrations of this type. Sheet 1 is a color photograph of Dragon grown as a single stem cut spray.

Sheet 2 comprises a first black and white photograph showing the foliage of Dragon at three stages of growth, and a second black and white photograph of three view of the inflorescence of Dragon.

In the following description color references are made to A Limit Color Cascade by the Munsell Company, 1972 edition. The color values were determined between 1:30 and 2:00 p.m. on Oct. 3, 1979 under 75 foot-candle light intensity at Salinas, Calif.

Classification:

*Botanical.*—*Chrysanthemum morifolium,* Ramat., cv Dragon.

*Commercial.*—Cut daisy spray.

I. Inflorescence:

A. *Capitulum.*—Form: flat. Type: Daisy. Diameter across face: 90 to 100 mm.

B. *Corolla of ray florets.*—General tonality (from a distance of three meters): Dark red, approximately 36-14 to 35-14. Color (abaxial): 38-15 to 38-14 oxidizing to 38-14 streaked over 34-14. Color (adaxial): 28-2 overlaid heavily with 38-14.

C. *Corolla of disc florets.*—Color (abaxial): Approximately 28-7. Color (adaxial): Approximately 22-10 (immature) to 28-6 (mature).

D. *Reproductive organs.*—Gynoecium: Present both ray and disc florets. Androecium: Present disc florets only; numerous; moderate to scant pollen.

II. Plant:

A. *General appearance.*—Height: Tall, attaining a height of 60 to 70 cm. as a flowered plant from a rooted cutting with no long days for May through October flowerings. Branching pattern: Semi-upright.

B. *Foliage.*—Color (abaxial): Approximately 20-15. Color (adaxial): Approximately 21-14 overlaid with white. Shape: Deeply lobed and coarsely serrated.

CHART A

COMPARISON OF DRAGON, FIREPOWER AND RED DAZZLER

| Cultivar | Ray Floret Color | Capitulum Form & Type | Diameter Across Face Of Capitulum | Plant Height | Flowering Response Period |
|---|---|---|---|---|---|
| Dragon | Dark Red | Flat Daisy | 90 to 100 mm. | Tall 60 to 70 cm. | 8 week |
| Firepower | Dark Red-Bronze | Flat Daisy | 70 to 75 mm. | Very Tall 75 to 80 cm. | 10 week |
| Red Dazzler | Bronze-red | Flat Daisy, Reflexing with Maturity | 85 to 95 mm. | Tall 60 to 70 cm. | 8 week |

COMPARISONS MADE OF PLANTS GROWN AS SINGLE STEM CUT SPRAYS WITH NO LONG DAYS IN SALINAS, CALIFORNIA.

We claim:

1. A new and distinct cultivar *Chrysanthemum morifolium,* Ramat., plant known by the cultivar name Dragon, as described and illustrated, and particularly characterized as to uniqueness by the combined characteristics of flat capitulum form; daisy capitulum type; dark red ray floret color with minimum color oxidation; yellow green (immature) to yellow (mature) disc floret color; diameter across face of capitulum ranging from 90 to 100 mm. at maturity; uniform eight week photoperiodic flowering response to short days; tall plant height when grown as a single stem cut spray; and semi-upright branching pattern.

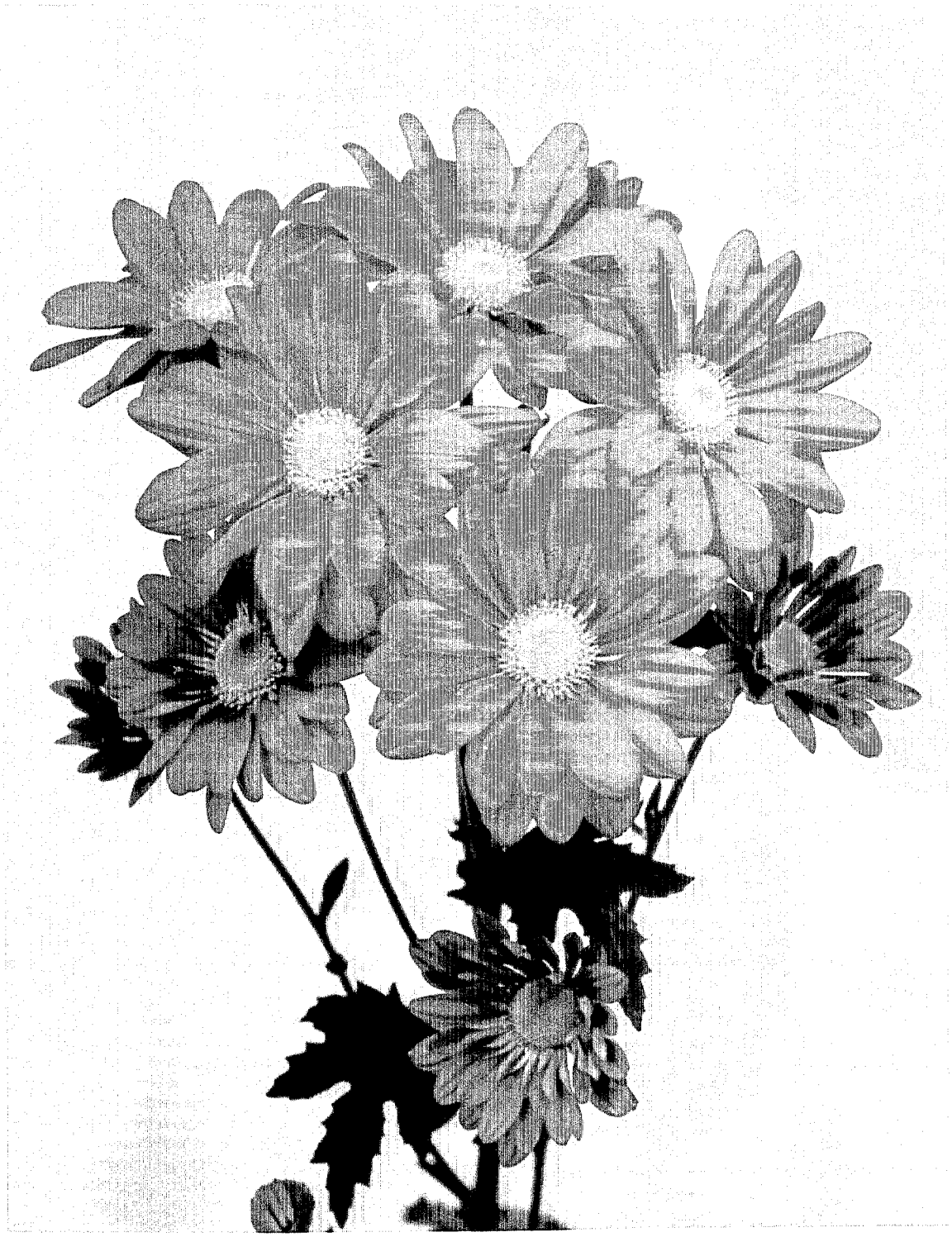

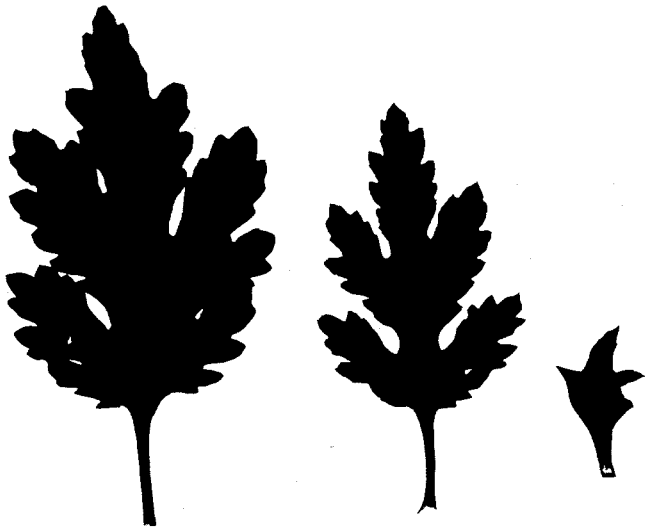
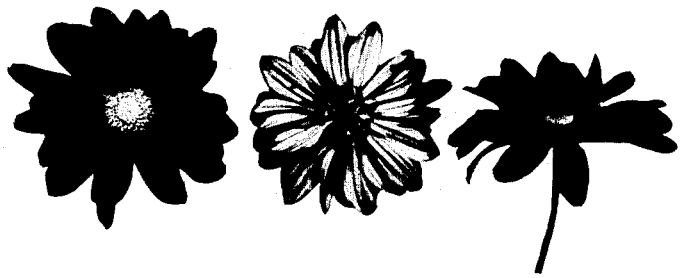

* * * * *